United States Patent
Lozano

(10) Patent No.: US 9,358,393 B1
(45) Date of Patent: Jun. 7, 2016

(54) STIMULATION METHODS AND SYSTEMS FOR TREATING AN AUDITORY DYSFUNCTION

(76) Inventor: Andres M. Lozano, Toronto (CA)

(*) Notice: Subject to any disclaimer, the term of this patent is extended or adjusted under 35 U.S.C. 154(b) by 1826 days.

(21) Appl. No.: 11/271,126

(22) Filed: Nov. 9, 2005

Related U.S. Application Data

(60) Provisional application No. 60/626,174, filed on Nov. 9, 2004.

(51) Int. Cl.
*A61N 1/00* (2006.01)
*A61B 5/02* (2006.01)
*A61N 1/36* (2006.01)
*A61N 1/05* (2006.01)

(52) U.S. Cl.
CPC .......... *A61N 1/36132* (2013.01); *A61N 1/0541* (2013.01)

(58) Field of Classification Search
USPC ........................................ 607/55, 57; 600/372
See application file for complete search history.

(56) References Cited

U.S. PATENT DOCUMENTS

| | | |
|---|---|---|
| 3,760,984 A | 9/1973 | Theeuwes |
| 3,845,770 A | 11/1974 | Theeuwes et al. |
| 3,916,899 A | 11/1975 | Theeuwes et al. |
| 3,923,426 A | 12/1975 | Theeuwes et al. |
| 3,987,790 A | 10/1976 | Eckenhoff et al. |
| 3,995,631 A | 12/1976 | Higuchi et al. |
| 4,016,880 A | 4/1977 | Theeuwes et al. |
| 4,036,228 A | 7/1977 | Theeuwes |
| 4,111,202 A | 9/1978 | Theeuwes |
| 4,111,203 A | 9/1978 | Theeuwes |
| 4,203,440 A | 5/1980 | Theeuwes |
| 4,203,442 A | 5/1980 | Michaels |
| 4,210,139 A | 7/1980 | Higuchi |

(Continued)

FOREIGN PATENT DOCUMENTS

WO    WO 01/08617 A1    2/2001

OTHER PUBLICATIONS

Office action dated Sep. 16, 2009 for related U.S. Appl. No. 11/271,688 (Lozano-1), filed Nov. 9, 2005, Inventor: Andres M. Lozano, (14 pages).

(Continued)

*Primary Examiner* — Nicole F Lavert
(74) *Attorney, Agent, or Firm* — Faegre Baker Daniels LLP

(57) ABSTRACT

Methods of treating auditory hallucinations, hyperacusis, schizophrenia, and/or phonophobia include applying at least one stimulus to a stimulation site within a patient with an implanted stimulator in accordance with one or more stimulation parameters. The stimulation site may include, for example, at least one or more of a cochlear nucleus, auditory striae, superior olivary complex, lateral lemniscus, inferior colliculus, brachium of the inferior colliculus, medial geniculate body, primary auditory cortex, secondary auditory cortical area, and auditory radiation. Systems for treating auditory hallucinations, hyperacusis, schizophrenia, and/or phonophobia include an implanted stimulator configured to apply at least one stimulus to a stimulation site within a patient in accordance with one or more stimulation parameters. The stimulation site may include, for example, at least one or more of a cochlear nucleus, auditory striae, superior olivary complex, lateral lemniscus, inferior colliculus, brachium of the inferior colliculus, medial geniculate body, primary auditory cortex, secondary auditory cortical area, and auditory radiation.

3 Claims, 9 Drawing Sheets

(56) References Cited

U.S. PATENT DOCUMENTS

| | | | |
|---|---|---|---|
| 4,284,856 A * | 8/1981 | Hochmair et al. | 607/9 |
| 4,327,725 A | 5/1982 | Cortese et al. | |
| 4,360,019 A | 11/1982 | Portner et al. | |
| 4,487,603 A | 12/1984 | Harris | |
| 4,562,751 A | 1/1986 | Nason et al. | |
| 4,627,850 A | 12/1986 | Deters et al. | |
| 4,678,408 A | 7/1987 | Nason et al. | |
| 4,685,903 A | 8/1987 | Cable et al. | |
| 4,692,147 A | 9/1987 | Duggan | |
| 4,725,852 A | 2/1988 | Gamblin et al. | |
| 4,865,845 A | 9/1989 | Eckenhoff et al. | |
| 5,057,318 A | 10/1991 | Magruder et al. | |
| 5,059,423 A | 10/1991 | Magruder et al. | |
| 5,069,210 A * | 12/1991 | Jeutter et al. | 607/57 |
| 5,080,653 A | 1/1992 | Voss et al. | |
| 5,097,122 A | 3/1992 | Colman et al. | |
| 5,112,614 A | 5/1992 | Magruder et al. | |
| 5,137,727 A | 8/1992 | Eckenhoff | |
| 5,193,539 A | 3/1993 | Schulman et al. | |
| 5,193,540 A | 3/1993 | Schulman et al. | |
| 5,234,692 A | 8/1993 | Magruder et al. | |
| 5,234,693 A | 8/1993 | Magruder et al. | |
| 5,312,439 A | 5/1994 | Loeb | |
| 5,496,369 A | 3/1996 | Howard, III | |
| 5,501,703 A | 3/1996 | Holsheimer et al. | |
| 5,676,655 A | 10/1997 | Howard, III et al. | |
| 5,697,975 A | 12/1997 | Howard, III et al. | |
| 5,713,847 A | 2/1998 | Howard, III et al. | |
| 5,728,396 A | 3/1998 | Peery et al. | |
| 5,735,885 A | 4/1998 | Howard, III et al. | |
| 5,776,172 A * | 7/1998 | Schulman et al. | 607/56 |
| 5,938,688 A | 8/1999 | Schiff | |
| 5,938,691 A * | 8/1999 | Schulman et al. | 607/57 |
| 5,975,085 A * | 11/1999 | Rise | 128/898 |
| 6,016,449 A | 1/2000 | Fischell et al. | |
| 6,051,017 A | 4/2000 | Loeb et al. | |
| 6,164,284 A | 12/2000 | Schulman et al. | |
| 6,176,242 B1 | 1/2001 | Rise | |
| 6,185,452 B1 | 2/2001 | Schulman et al. | |
| 6,208,894 B1 | 3/2001 | Schulman et al. | |
| 6,214,046 B1 * | 4/2001 | Kennedy | 623/10 |
| 6,216,040 B1 * | 4/2001 | Harrison | 607/57 |
| 6,219,580 B1 * | 4/2001 | Faltys et al. | 607/57 |
| 6,272,382 B1 * | 8/2001 | Faltys et al. | 607/57 |
| 6,289,247 B1 * | 9/2001 | Faltys et al. | 607/57 |
| 6,308,101 B1 | 10/2001 | Faltys et al. | |
| 6,368,315 B1 | 4/2002 | Gillis et al. | |
| 6,381,496 B1 | 4/2002 | Meadows et al. | |
| 6,390,971 B1 * | 5/2002 | Adams et al. | 600/25 |
| 6,430,443 B1 * | 8/2002 | Karell | 607/55 |
| 6,456,886 B1 * | 9/2002 | Howard et al. | 607/55 |
| 6,487,446 B1 | 11/2002 | Hill et al. | |
| 6,516,227 B1 | 2/2003 | Meadows et al. | |
| 6,539,263 B1 | 3/2003 | Schiff et al. | |
| 6,553,263 B1 | 4/2003 | Meadows et al. | |
| 6,572,531 B2 * | 6/2003 | Zilberman et al. | 600/25 |
| 6,620,151 B2 | 9/2003 | Blischak | |
| 6,656,172 B1 | 12/2003 | Hildebrand | |
| 6,666,845 B2 | 12/2003 | Hooper et al. | |
| 6,732,073 B1 * | 5/2004 | Kluender et al. | 704/233 |
| 6,740,072 B2 | 5/2004 | Starkweather et al. | |
| 6,760,626 B1 | 7/2004 | Boveja | |
| 6,770,067 B2 | 8/2004 | Lorenzen et al. | |
| 6,915,166 B1 * | 7/2005 | Stecker et al. | 607/55 |
| 6,993,392 B2 * | 1/2006 | Nicolelis et al. | 607/45 |
| 7,292,892 B2 * | 11/2007 | Litvak et al. | 607/57 |
| 2004/0236390 A1 * | 11/2004 | Dadd et al. | 607/55 |
| 2005/0070971 A1 * | 3/2005 | Fowler et al. | 607/45 |
| 2006/0217784 A1 * | 9/2006 | Kitazawa et al. | 607/57 |
| 2007/0043403 A1 * | 2/2007 | Blamey et al. | 607/55 |
| 2007/0106344 A1 * | 5/2007 | Darley et al. | 607/55 |
| 2007/0129772 A1 * | 6/2007 | Loeb | 607/57 |
| 2007/0255344 A1 * | 11/2007 | Van Dijk | 607/57 |

OTHER PUBLICATIONS

Office Action dated May 25, 2010 for related U.S. Appl. No. 11/271,688 (Lozano-1), filed Nov. 9, 2005, Inventor: Andres M. Lozano, (9 pages).

Office Action dated Aug. 10, 2010 for related U.S. Appl. No. 11/271,688 (Lozano-1), filed Nov. 9, 2005, Inventor: Andres M. Lozano, (5 pages).

Non-Final Office Action dated Apr. 1, 2008 issued from related U.S. Appl. No. 11/271,688; Inventor: Andres M. Lozano (12 pages).

Adams DA, Wilmont TJ. Meniere's disease: long-term results of sympathectomy. J Laryngol Otol 1982; 96:705-10.

De Ridder D, De Mulder G, Walsh V, Muggleton N, Sunaert S, Moller A. Magnetic and electrical stimulation of the auditory cortex for intractable tinnitus. Case report. J Neuros.

Heller AJ. Classification and epidemiology of tinnitus. Otolaryngol Clin North Am 2003; 36:239-48.

Ito J, Sakakihara J. Suppression of tinnitus by cochlear implantation. Am J Otolaryngol 1994; 15:145-8.

Jastreboff PJ, Jastreboff MM. Tinnitus retraining therapy for patients with tinnitus and decreased sound tolerance. Otolaryngol Clin North Am 2003; 36:321-36.

Johnson RM, Brummett R, Schleuning A. Use of alprazolam for relief of tinnitus. A double-blind study. Arch Otolaryngol Head Neck Surg 1993; 119:842-5.

Moller AR. Pathophysiology of tinnitus. Otolaryngol Clin North Am 2003; 36:249-66, v-vi.

Moller AR. Similarities between severe tinnitus and chronic pain. J Am Acad Audiol 2000; 11:115-24.

Moller MB, Moller AR, Jannetta PJ, Jho HD. Vascular decompression surgery for severe tinnitus: selection criteria and results. Laryngoscope 1993; 103:421-7.

Schleuning AJ, Johnson RM, Vernon JA. Evaluation of a tinnitus masking program: a follow-up study of 598 patients. Ear Hear 1980; 1:71-4.

Schleuning AJ, Johnson RM. Use of Masking for Tinnitus. Int Tinnitus J 1997; 3:25-29.

Seidman MD, Babu S. Alternative medications and other treatments for tinnitus: facts from fiction. Otolaryngol Clin North Am 2003; 36:359-81.

Sterrnerson RL, Cronin GW. Tinnitus reduction using transcutaneous electrical stimulation. Otolaryngol Clin North Am 2003; 36:337-44.

Tasker RR. Auditory system. In: Tasker RR, ed. The thalamus and midbrain of man : a physiological atlas using electrical stimulation: C.C. Thomas, 1982:200-215.

Vernon JA, Meikle MB. Masking devices and alprazolam treatment for tinnitus. Otolaryngol Clin North Am 2003; 36:307-20, vii.

Office Action dated Mar. 4, 2009, for U.S. Appl. No. 11/271,688, Inventor: Andres M. Lozano, (Lozano-1) (12 pages).

* cited by examiner

STIMULATION METHODS AND SYSTEMS FOR TREATING AN AUDITORY DYSFUNCTION

RELATED APPLICATIONS

The present application claims the priority under 35 U.S.C. §119 (e) of previous U.S. Provisional Patent Application No. 60/626,174 filed Nov. 9, 2004 for "Stimulation Methods to Treat Auditory Dysfunction." This provisional application is hereby incorporated by reference in its entirety.

BACKGROUND

Auditory dysfunction is a broad term that includes a variety of conditions affecting and relating to the human auditory system including, for example, auditory hallucinations, hyperacusis, phonophobia, tinnitus, hearing loss, etc. In general, the public health significance of many auditory dysfunctions is often overlooked. Some auditory dysfunctions are often incapacitating, with considerable impact on social activities and work.

Among the various types of auditory dysfunctions, auditory hallucinations are particularly disabling. People who suffer from auditory hallucinations hear voices, sounds, or noises that are not actually occurring. Many people with auditory hallucinations perceive, for example, recognizable voices which utter comprehensible phrases. Other auditory hallucinations range from primitive noises such as bangs, whistles, claps, screams, and ticks to speech and music.

Auditory hallucinations affect millions of people worldwide. The disorder can cause distress, functional disability, and problems in behavior. Those who suffer from auditory hallucinations often have difficulty sleeping and performing intellectual work. Auditory hallucinations can ultimately lead to depression, the disruption of familial and social activities, or even suicide.

Auditory hallucinations (particularly of one or more talking voices) are often associated with psychotic disorders such as schizophrenia. Schizophrenia is a chronic, severe, and disabling brain disease. Approximately one percent of the population develops schizophrenia during their lifetime. More than two million Americans suffer from the illness in a given year.

One of the symptoms often seen in many schizophrenia patients is the occurrence of auditory hallucinations. These hallucinations may cause them to believe that other people are reading their minds, controlling their thoughts, or plotting to harm them and can leave them fearful and withdrawn. Their resulting speech and behavior can be so disorganized that they may be incomprehensible or frightening to others.

Several strategies have been proposed to treat patients with auditory dysfunctions. Pharmacological treatment has been tried in many patients. However, it has been found that some auditory dysfunctions are often resistant to drug treatment. Psychological therapy has been successful to some extent. Other techniques, such as biofeedback, cognitive therapy, and repetitive transcranial magnetic stimulation (rTMS) have also been tried with varied results. Despite the various procedures described above, there are still patients with auditory dysfunctions who continue to be refractory to treatment.

SUMMARY

Methods of treating auditory hallucinations, hyperacusis, schizophrenia, and/or phonophobia include applying at least one stimulus to a stimulation site within a patient with an implanted stimulator in accordance with one or more stimulation parameters. The stimulation site may include, for example, at least one or more of a cochlear nucleus, auditory striae, superior olivary complex, lateral lemniscus, inferior colliculus, brachium of the inferior colliculus, medial *geniculate* body, primary auditory cortex, secondary auditory cortical area, and auditory radiation.

Systems for treating auditory hallucinations, hyperacusis, schizophrenia, and/or phonophobia include an implanted stimulator configured to apply at least one stimulus to a stimulation site within a patient in accordance with one or more stimulation parameters. The stimulation site may include, for example, at least one or more of a cochlear nucleus, auditory striae, superior olivary complex, lateral lemniscus, inferior colliculus, brachium of the inferior colliculus, medial *geniculate* body, primary auditory cortex, secondary auditory cortical area, and auditory radiation.

BRIEF DESCRIPTION OF THE DRAWINGS

The accompanying drawings illustrate various embodiments of the present invention and are a part of the specification. The illustrated embodiments are merely examples of the present invention and do not limit the scope of the invention.

Throughout the drawings, identical reference numbers designate similar, but not necessarily identical, elements.

DETAILED DESCRIPTION

Figure 1A:
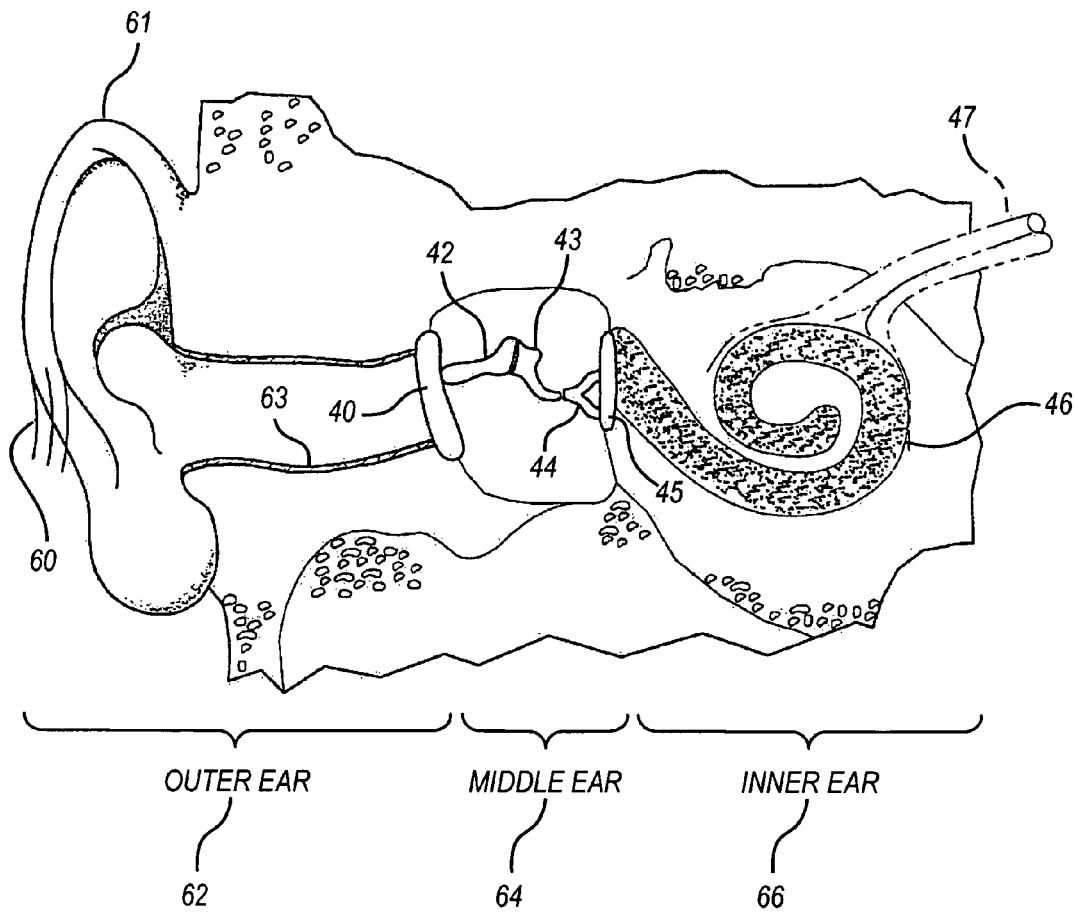
FIG. 1A shows a representation of a human auditory system divided into the outer, middle and inner ear.

Methods and systems for treating auditory dysfunctions such as auditory hallucinations, hyperacusis, schizophrenia, and/or phonophobia are described herein. An implanted stimulator is configured to apply at least one stimulus to a stimulation site along the auditory pathway of a patient in accordance with one or more stimulation parameters. The stimulus is configured to treat the auditory dysfunction and may include electrical stimulation, drug stimulation, chemical stimulation, thermal stimulation, electromagnetic stimulation, mechanical stimulation, and/or any other suitable stimulation. The stimulation sites that may be stimulated may include, for example, at least one or more of a cochlear nucleus, auditory striae, superior olivary complex, lateral lemniscus, inferior colliculus, brachium of the inferior colliculus, medial geniculate body, primary auditory cortex, secondary auditory cortical area, and auditory radiation.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

As used herein and in the appended claims, unless otherwise specifically denoted, the term "auditory pathway" refers to both the mechanical and neural structures that transduce audible sound into an electrical signal and convey that signal to the brain. The mechanical portion of the auditory pathway includes the outer, middle and inner portions of the ear. The neural portion of the auditory pathway includes any axons, ganglion, nerve, fibers, nuclei, etc. that transmit or relay sound information. The neural portion of the auditory pathway begins at the spiral ganglion of the cochlea in the auditory nerve which synapses in the cochlear nuclei at the junction of the medulla and pons. The pons is a knob on the brain stem and relays sensory information between the cerebellum and cerebrum. From the cochlear nuclei, the secondary auditory neurons send most of their axons across the midline to ascend in the contralateral lemniscus. The fibers that cross the midline from the ventral cochlear nucleus form the trapezoid body. Some of these crossing fibers synapse in cells embedded within the trapezoid body and others synapse in the contralateral superior olivary nucleus before joining the lateral lemniscus. Still further, a small number of uncrossed fibers synapse in the ipsilateral superior olivary nucleus where they ascend in the ipsilateral lateral lemniscus. The lateral lemniscus ascends in the tegmentum of the pons and midbrain and terminates in the inferior colliculus. The axons of the inferior colliculus then travel through the brachium of the inferior colliculus to the medial geniculate body of the thalamus. Next, the thalamic neurons project through the internal capsule to terminate in the transverse gyri of Heschl of the auditory cortex, which is where the conscious perception of sound occurs.

Also, as used herein and in the appended claims, unless otherwise specifically denoted, the term "auditory dysfunction" refers to a condition or dysfunction associated with the auditory pathway. Such auditory dysfunctions may include, but are not limited to auditory hallucinations, hyperacusis, phonophobia, schizophrenia, and tinnitus. Auditory hallucinations can occur in schizophrenia or with the use of certain drugs (e.g., antimuscarinic agents, antiparkinsonian drugs, antidepressants, beta adrenoceptor antagonists and opiates). Another auditory dysfunction is hearing loss. Hearing loss may be conductive hearing loss (where mechanical transmission of sound into the sensory receptors in the cochlea is impaired), sensorineural hearing loss (where there is a loss of function in the sensory receptors in either the cochlea or the auditory nerve), or central hearing loss (where there is a lesion in the brain stem or auditory cortex).

FIG. 1A shows a representation of a human auditory system divided into the outer, middle and inner ear. It is instructive to review the operation of the normal auditory apparatus in order to discuss the treatment of auditory dysfunctions. As shown, sound waves (60) are collected by the auricle (61) of the outer ear (62). The collected sound waves (60) then pass through the ear canal (63) and strike the eardrum or typmpanic membrane (40) causing it to vibrate in accordance with the frequencies and intensity of the sound waves (60). In a functioning ear, this creates a chain reaction in the three tiny bones in the middle ear (64). These bones are the malleus (42), the incus (43), and the stapes (44). Movement of these bones, in turn, generates movement of the round window (45), causing vibrations in the fluid contained in the cochlea (46). The cochlea (46) is located in the inner ear (66).

Figure 1B:
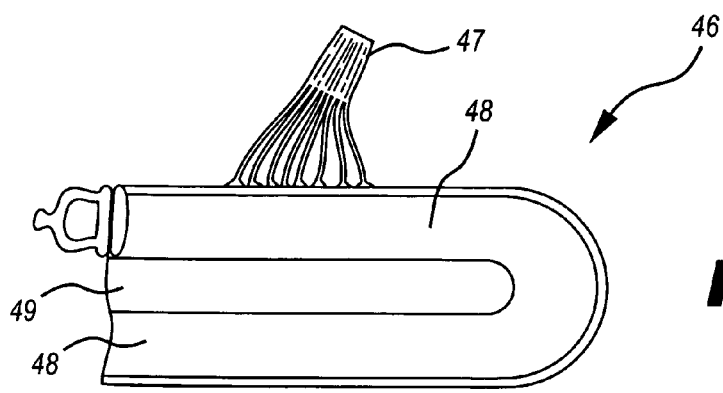
FIG. 1B shows the cochlea of FIG. 1A as it would appear uncoiled.

FIG. 1B shows the cochlea (46) of FIG. 1A as it would appear uncoiled. The cochlea (46) is divided into two fluid-filled chambers (48) separated by the organ of Corti (49). Vibrations in the fluid cause mechanical stimulation of sensory receptor cells known as hair cells on the organ of Corti (49). This mechanical stimulation causes ion channels on the hair cells to open, altering their membrane potential and changing the release rate of a synaptic neurotransmitter. Afferent nerve fibers from the auditory nerve (47) take up the neurotransmitter and an action potential in the nerve fibers may be generated depending on the quantity of released neurotransmitter.

Figure 2:
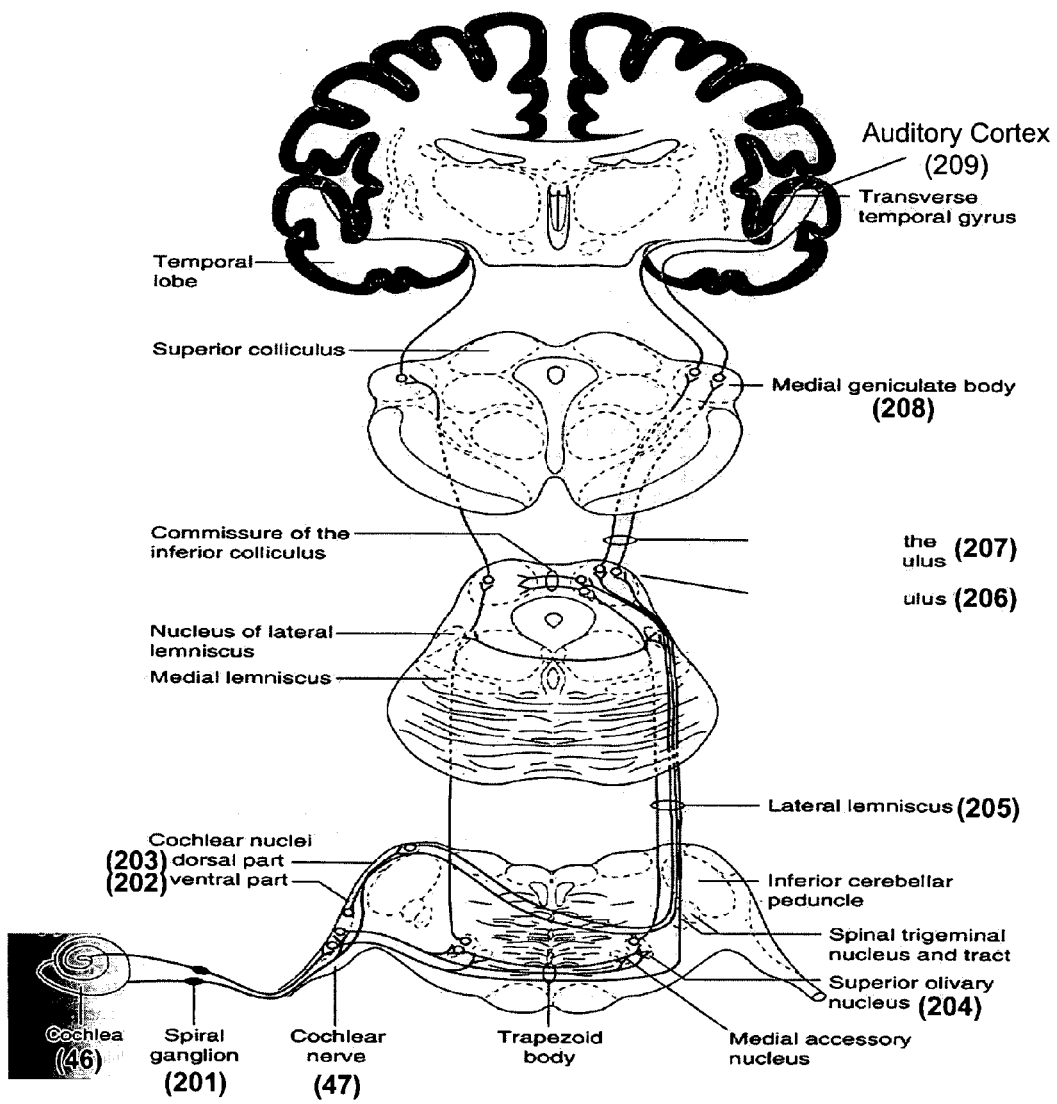
FIG. 2 is an illustration of connections in the auditory pathway.

As used herein, the terms "auditory nerve" and "cochlear nerve" are interchangeable and refer to the nerve fibers along which the sensory cells of the ear communicate information to the brain. Referring now to FIG. 2, the auditory nerve (47) connects to two separate pathways after leaving the cochlea (46). Primary axons in synaptic contact with the hair cells of the organ of Corti (49; FIG. 1B) have their cell bodies in the spiral ganglion (201) and enter the brainstem at the juncture of the pons and cerebellum. Here, each axon bifurcates and synapses in the dorsal and ventral cochlear nuclei (202, 203) of the medulla. Second order axons from the dorsal and ventral cochlear nuclei (202, 203) may synapse in the superior olivary nucleus (204) or may pass directly to the nucleus of the inferior colliculus (206) via the lateral lemniscus (205). These connections may be made both ipsilaterally and contralaterally. From the inferior colliculus (206), axons project along the brachium of the inferior colliculus (207) and reach the medial geniculate body (208) of the thalamus. The thalamocortical auditory projection runs from the medial geniculate body (208) (also known as the medial geniculate nucleus) to the auditory cortex (209).

Figure 3:
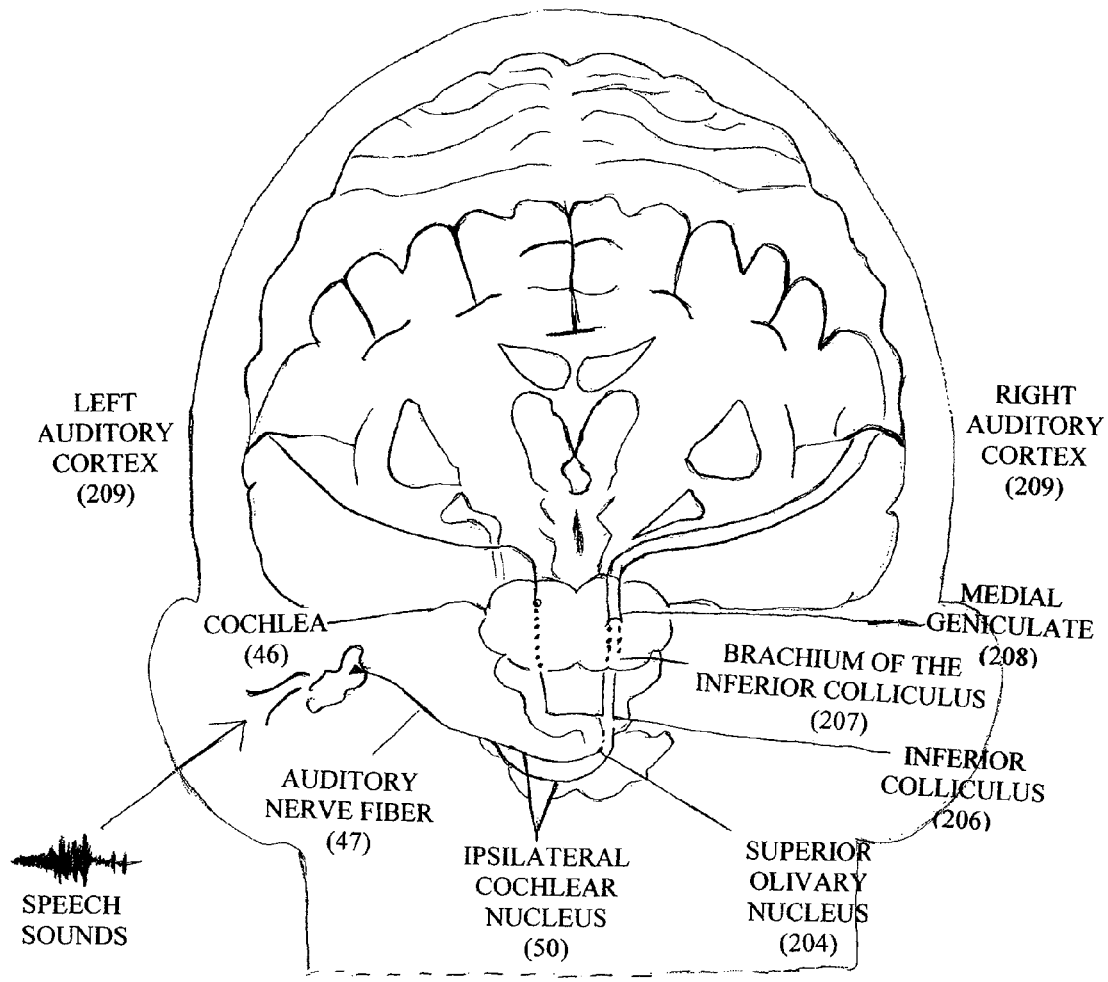
FIG. 3 shows another view of the auditory pathway as viewed from the back of the head.

FIG. 3 shows another view of the auditory pathway as viewed from the back of the head and shows the cochlea (46), auditory nerve (47), ipsilateral cochlear nucleus (50), superior olivary nucleus (204), inferior colliculus (206), brachium of the inferior colliculus (207), medial geniculate nucleus (208), and auditory cortex (209).

The brachium of the inferior colliculus (207) refers to the neuronal tissue, such as the axons, extending from the inferior colliculus (206) to the medial geniculate body (208). The brachium of the inferior colliculus (207) can include the defined area of the brachium of the inferior colliculus (207), as well as the surrounding or adjacent white matter tracts leading to and from the brachium of the inferior colliculus (207) and/or white matter tracts that are contiguous with the brachium of the inferior colliculus (207).

The superior olivary complex (SOC) (204) includes the medial nucleus of the superior olive, the lateral nucleus of the superior olive, and the medial nucleus of the trapezoid body. The SOC also includes a number of pre-olivary and peri-olivary nuclei which receive mostly efferent innervation.

The inferior colliculus (206) includes the surrounding or adjacent white matter tracts leading to and from the inferior colliculus (206). Specifically, the inferior colliculus (206)

includes the fibers leading to the medial geniculate nucleus and/or white matter tracts that are contiguous with inferior colliculus (206). The inferior colliculus (206) receives information from the lateral lemniscus and projects this information via the brachium of the inferior colliculus (207) to the medial geniculate body (208). Thus, stimulation of the inferior colliculus (208) can result in neuronal alterations in any of the fibers along this pathway from the inferior colliculus (206) to the medial geniculate body (208). Similarly, stimulation of the axons in the brachium of the inferior colliculus (206) can result in neuronal alterations in the medial geniculate body (208) and in downstream auditory pathways.

Brain imaging studies suggest that many auditory dysfunctions arise from parts of the brain that are ordinarily involved in perceiving verbal speech. Consequently, a stimulator may be implanted in a patient to deliver a stimulus to one or more stimulation sites along the auditory pathway in the brain to treat auditory dysfunctions such as auditory hallucinations, hyperacusis, and/or phonophobia. As used herein and in the appended claims, the term "stimulation site" will be used to refer to any area within the auditory pathway including, but not limited to, the cochlear nuclei, auditory striae, superior olivary complex, lateral lemniscus, inferior colliculus, brachium of the inferior colliculus, medial geniculate body, primary auditory cortex, secondary auditorial cortical areas, and auditory radiations (the fibers or projections that extend from the medial geniculate body to the auditory cortex). Any of these stimulation sites may be localized by their known anatomical locations and can be identified in individual patients by examining areas of brain change, activation or inactivation in response to auditory stimuli using functional imaging (e.g., magnetic resonance imaging (MRI), magnetoencephalography (MEG) and positron emission tomography (PET)), and evoked potentials or changes in the electroencephalogram.

The stimulation may be effective to treat auditory hallucinations, hyperacusis, and phonophobia. The present specification will describe methods and systems for implanting such a stimulator to most conveniently treat a variety of auditory dysfunctions, particularly auditory hallucinations, hyperacusis, and/or phonophobia.

As used herein, and in the appended claims, the term "stimulator" will be used broadly to refer any device that delivers a stimulus, such as an electrical stimulation current, one or more drugs or other chemical stimulation, thermal stimulation, electromagnetic stimulation, mechanical stimulation, and/or any other suitable stimulation to a stimulation site. Thus, the term "stimulator" includes, but is not limited to, a stimulator, microstimulator, implantable pulse generator (IPG), system control unit (SCU), or similar device.

Figure 4:
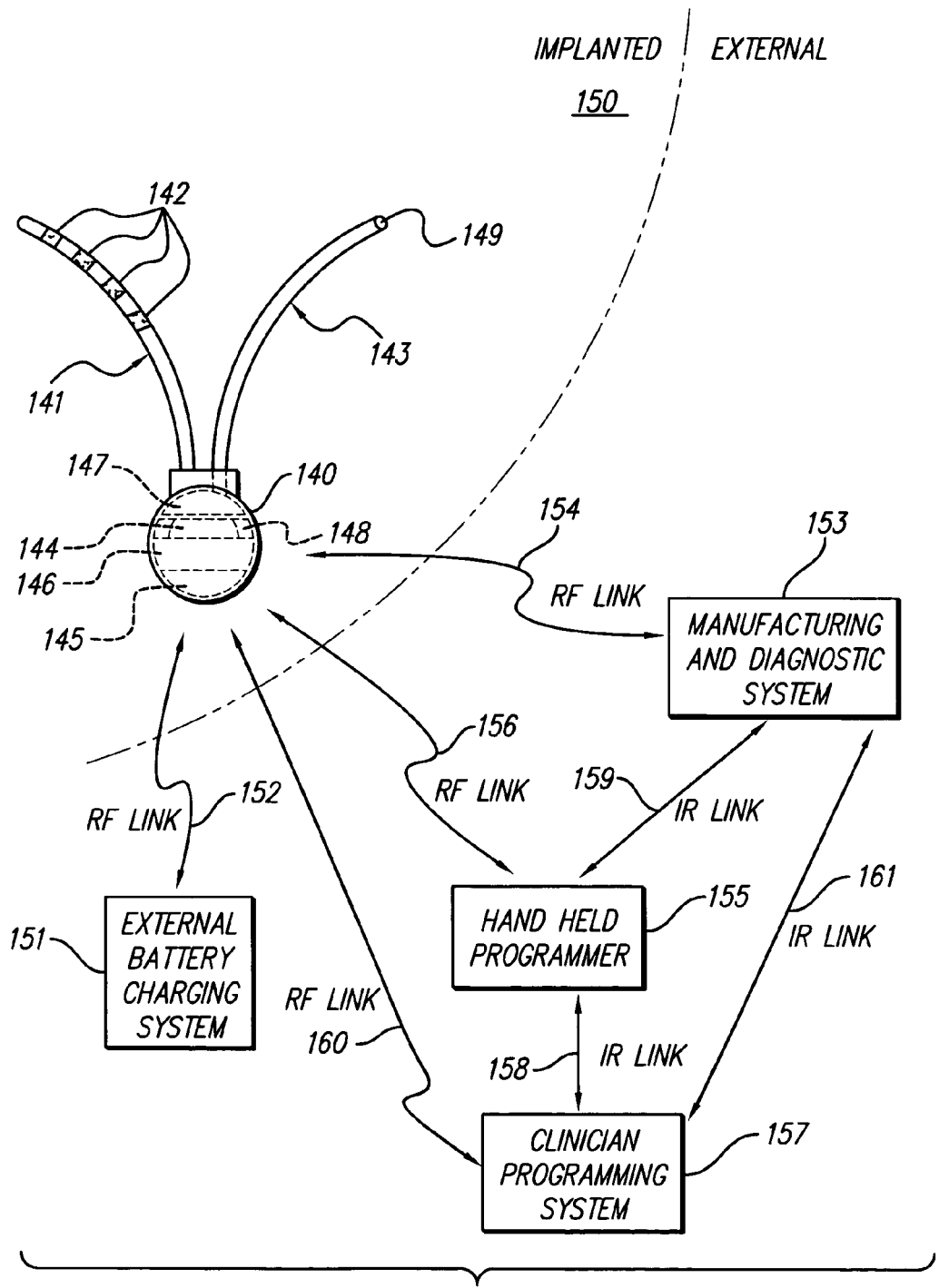
FIG. 4 illustrates an exemplary stimulator that may be used to apply a stimulus to a target nerve to treat a particular medical condition according to principles described herein.

To facilitate an understanding of the methods of optimally placing a stimulator to treat an auditory dysfunction, as described herein, a more detailed description of the stimulator and its operation will now be given with reference to the figures. FIG. 4 illustrates an exemplary stimulator (140) that may be implanted within a patient (150) and used to apply a stimulus to a stimulation site, e.g., an electrical stimulation of the stimulation site, an infusion of one or more drugs into the stimulation site, or both. The electrical stimulation function of the stimulator (140) will be described first, followed by an explanation of the drug delivery function of the stimulator (140). It will be understood, however, that the stimulator (140) may be configured to provide any type of stimulation as best suits a particular patient.

The exemplary stimulator (140) shown in FIG. 4 is configured to provide electrical stimulation to a stimulation site within a patient and includes a lead (141) having a proximal end coupled to the body of the stimulator (140). The lead (141) also includes a number of electrodes (142) configured to apply an electrical stimulation current to a stimulation site. In some embodiments, the lead (141) includes anywhere between two and sixteen electrodes (142). However, the lead (141) may include any number of electrodes (142) as best serves a particular application. The electrodes (142) may be arranged as an array, for example, having at least two or at least four collinear electrodes. In some embodiments, the electrodes are alternatively inductively coupled to the stimulator (140). The lead (141) may be thin (e.g., less than 3 millimeters in diameter) such that the lead (141) may be positioned near a stimulation site.

FIGS. 5A-5D illustrate a number of exemplary electrical stimulation leads (141) that may be used to provide electrical stimulation to an area of the brain. As described above, each of the one or more leads (141) includes one or more electrodes (142) adapted to be positioned near the stimulation site and used to deliver electrical stimulation energy to the stimulation site in response to electrical signals generated by the stimulator (140; FIG. 4). A percutaneous lead, such as the exemplary leads (141) shown in FIGS. 5A-5D, may include one or more circumferential electrodes (142) spaced apart from one another along the length of the lead (141). Circumferential electrodes (142) emit electrical stimulation energy generally radially in all directions.

Figure 5A:
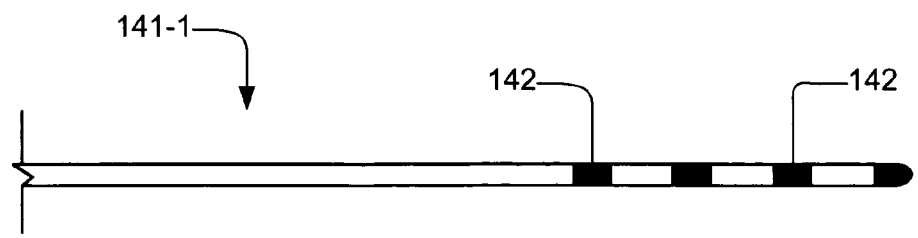
FIGS. 5A-5D illustrate a number of exemplary electrical stimulation leads that may be used to provide electrical stimulation to an area of the brain according to principles described herein.
Figure 5B:
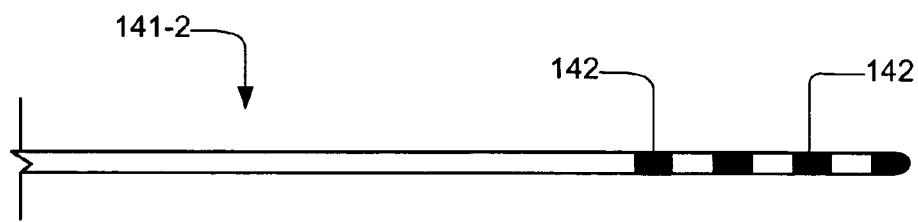
Figure 5C:
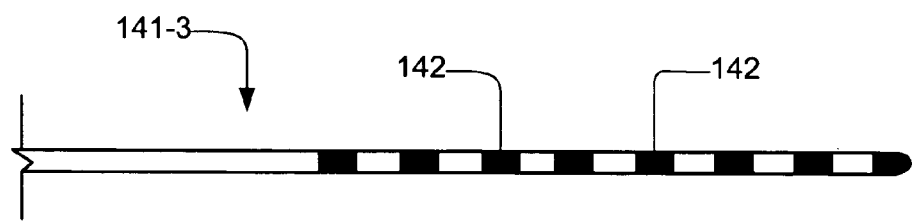
Figure 5D:
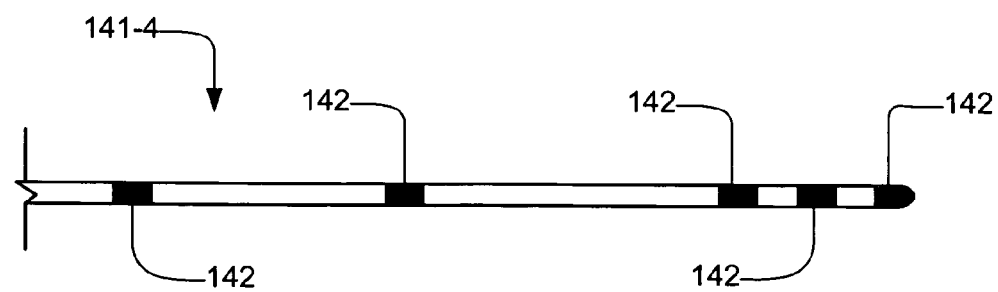

As shown in FIGS. 5A-5C, the electrodes (142) may be evenly spaced along a portion of the lead (141). However, as shown in FIG. 5D, the electrodes (142) may not be evenly spaced along the lead (141), but may be distributed in any configuration that best suits a particular application. Also as shown in FIGS. 5A-5D, the electrodes (141) may be distributed only along the distal or some other portion of the lead (141), along the majority of the length of the lead (141) or along substantially the entire length of the lead (141).

In some alternative examples, the lead (141) includes one or more substantially flat sides upon which the electrodes (142) are disposed. Such an electrode arrangement is advantageous in many applications where it is desirable for the electrical stimulation energy to be more efficiently directed towards a particular stimulation site.

With reference again to FIG. 4, the stimulator (140) includes a number of components. It will be recognized that the stimulator (140) may include additional and/or alternative components as best serves a particular application. A power source (145) is configured to output voltage used to supply the various components within the stimulator (140) with power and/or to generate the power used for electrical stimulation. The power source (145) may be a primary battery, a rechargeable battery, super capacitor, a nuclear battery, a mechanical resonator, an infrared collector (receiving, e.g., infrared energy through the skin), a thermally-powered energy source (where, e.g., memory-shaped alloys exposed to a minimal temperature difference generate power), a flexural powered energy source (where a flexible section subject to flexural forces is part of the stimulator), a bioenergy power source (where a chemical reaction provides an energy source), a fuel cell, a bioelectrical cell (where two or more electrodes use tissue-generated potentials and currents to capture energy and convert it to useable power), an osmotic pressure pump (where mechanical energy is generated due to fluid ingress), or the like. Alternatively, the stimulator (140) may include one or more components configured to receive power from another medical device that is implanted within the patient.

The stimulator (140) may also include a coil (148) configured to receive and/or emit a magnetic field (also referred to as a radio frequency (RF) field) that is used to communicate with or receive power from one or more external devices (151, 153, 155). Such communication and/or power transfer may include, but is not limited to, transcutaneously receiving data from the external device, transmitting data to the external device, and/or receiving power used to recharge the power source (145).

For example, an external battery charging system (EBCS) (151) may provide power used to recharge the power source (145) via an RF link (152). External devices including, but not limited to, a hand held programmer (HHP) (155), clinician programming system (CPS) (157), and/or a manufacturing and diagnostic system (MDS) (153), may be configured to activate, deactivate, program, and test the stimulator (140) via one or more RF links (154, 156). It will be recognized that the links, which are RF links (152, 154, 156) in the illustrated example, may be any type of link used to transmit data or energy, such as an optical link, a thermal link, or any other energy-coupling link. One or more of these external devices (153, 155, 157) may also be used to control the infusion of one or more drugs into a stimulation site to treat an auditory dysfunction.

Additionally, if multiple external devices are used in the treatment of a patient, there may be some communication among those external devices, as well as with the implanted stimulator (140). Again, any type of link for transmitting data or energy may be used among the various devices illustrated. For example, the CPS (157) may communicate with the HHP (155) via an infrared (IR) link (158), with the MDS (153) via an IR link (161), and/or directly with the stimulator (140) via an RF link (160). As indicated, these communication links (158, 161, 160) are not necessarily limited to IR and RF links and may include any other type of communication link. Likewise, the MDS (153) may communicate with the HHP (155) via an IR link (159) or via any other suitable communication link.

The HHP (155), MDS (153), CPS (157), and EBCS (151) are merely illustrative of the many different external devices that may be used in connection with the stimulator (140). Furthermore, it will be recognized that the functions performed by any two or more of the HHP (155), MDS (153), CPS (157), and EBCS (151) may be performed by a single external device. One or more of the external devices (153, 155, 157) may be embedded in a seat cushion, mattress cover, pillow, garment, belt, strap, pouch, or the like so as to be positioned near the implanted stimulator (140) when in use.

The stimulator (140) may also include electrical circuitry (144) configured to produce electrical stimulation pulses that are delivered to the stimulation site via the electrodes (142). In some embodiments, the stimulator (140) may be configured to produce monopolar stimulation. The stimulator (140) may alternatively or additionally be configured to produce bipolar or tripolar stimulation. Monopolar electrical stimulation is achieved, for example, by using two electrodes spaced relatively far apart. Bipolar and tripolar electrical stimulation is achieved, for example, by using two or three electrodes that are relatively close to one another. The electrical circuitry (144) may include one or more processors configured to decode stimulation parameters and generate the stimulation pulses. In some embodiments, the stimulator (140) has at least four channels and drives up to sixteen electrodes or more. The electrical circuitry (144) may include additional circuitry such as capacitors, integrated circuits, resistors, coils, and the like configured to perform a variety of functions as best serves a particular application.

The stimulator (140) may also include a programmable memory unit (146) for storing one or more sets of data and/or stimulation parameters. The stimulation parameters may include, but are not limited to, electrical stimulation parameters, drug stimulation parameters, and other types of stimulation parameters. The programmable memory (146) allows a patient, clinician, or other user of the stimulator (140) to adjust the stimulation parameters such that the stimulation applied by the stimulator (140) is safe and efficacious for treatment of a particular auditory dysfunction. The different types of stimulation parameters (e.g., electrical stimulation parameters and drug stimulation parameters) may be controlled independently. However, in some instances, the different types of stimulation parameters are coupled. For example, electrical stimulation may be programmed to occur only during drug stimulation. Alternatively, the different types of stimulation may be applied at different times or with only some overlap. The programmable memory (146) may be any type of memory unit such as, but not limited to, random access memory (RAM), static RAM (SRAM), a hard drive, or the like.

The electrical stimulation parameters may control various parameters of the stimulation current applied to a stimulation site including, but not limited to, the frequency, pulse width, amplitude, electrode configuration (i.e., anode-cathode assignment), burst pattern (e.g., burst on time and burst off time), duty cycle or burst repeat interval, ramp on time, and ramp off time of the stimulation current that is applied to the stimulation site. The drug stimulation parameters may control various parameters including, but not limited to, the amount of drugs infused into the stimulation site, the rate of drug infusion, and the frequency of drug infusion. For example, the drug stimulation parameters may cause the drug infusion rate to be intermittent, constant, or bolus. Other stimulation parameters that characterize other classes of stimuli are possible. For example, when tissue is stimulated using electromagnetic radiation, the stimulation parameters may characterize the intensity, wavelength, and timing of the electromagnetic radiation stimuli. When tissue is stimulated using mechanical stimuli, the stimulation parameters may characterize the pressure, displacement, frequency, and timing of the mechanical stimuli.

Specific stimulation parameters may have different effects on different types of auditory dysfunctions. Thus, in some embodiments, the stimulation parameters may be adjusted by the patient, a clinician, or other user of the stimulator (140) as best serves a particular medical condition. The stimulation parameters may also be automatically adjusted by the stimulator (140), as will be described below. For example, the amplitude of the stimulus current applied to a stimulation site may be adjusted to have a relatively low value to target relatively large diameter fibers of a stimulation site. The stimulator (140) may also increase excitement of a stimulation site by applying a stimulation current having a relatively low frequency to the stimulation site (e.g., less than 100 Hz). The stimulator (140) may also decrease excitement of a stimulation site by applying a relatively high frequency to the stimulation site (e.g., greater than 100 Hz). The stimulator (140) may also be programmed to apply the stimulation current to a stimulation site intermittently or continuously.

An exemplary set of stimulation parameters that may be used to treat an auditory dysfunction will now be described. It will be recognized that the following stimulation parameters are merely illustrative and may be modified as best serves a particular auditory dysfunction or stimulation site. In some examples, the stimulation site is stimulated with a stimulation current having a pulse width of about 1 to about 500 microseconds, a frequency of about 1 to about 300 Hz, and a voltage of about 0.5 to about 10 volts.

Additionally, the exemplary stimulator (140) shown in FIG. 4 may be configured to provide drug stimulation to a patient, for example, a patient suffering from an auditory dysfunction, by applying one or more drugs to a stimulation site. For this purpose, a pump (147) may also be included within the stimulator (140). The pump (147) is configured to store and dispense one or more drugs, for example, through a catheter (143). The catheter (143) is coupled at a proximal end to the stimulator (140) and may have an infusion outlet (149) for infusing dosages of the one or more drugs at a stimulation site. In some embodiments, the stimulator (140) may include multiple catheters (143) and/or pumps (147) for storing and infusing dosages of the one or more drugs at the stimulation site.

The one or more drugs may applied to the stimulation site may include, but are not limited to, medications, anesthetic agents, synthetic or natural peptides or hormones, neurotransmitters, cytokines and other intracellular and intercellular chemical signals and messengers, and the like. In addition, certain neurotransmitters, hormones, and other drugs are excitatory for some tissues, yet are inhibitory to other tissues. Therefore, where a drug is referred to herein as an "excitatory" drug, this means that the drug is acting in an excitatory manner in the described application, although the same drug may act in an inhibitory manner in other circumstances and/or locations. Similarly, where an "inhibitory" drug is mentioned, this drug is acting in an inhibitory manner in the described application, although in other circumstances and/or locations, it may be an "excitatory" drug. In addition, stimulation of an area herein includes stimulation of cell bodies and axons in the area.

Similarly, excitatory neurotransmitter agonists (e.g., norepinephrine, epinephrine, glutamate, acetylcholine, serotonin, dopamine), agonists thereof, and agents that act to increase levels of an excitatory neurotransmitter(s) (e.g., edrophonium; Mestinon; trazodone; SSRIs (e.g., flouxetine, paroxetine, sertraline, citalopram and fluvoxamine); tricyclic antidepressants (e.g., imipramine, amitriptyline, doxepin, desipramine, trimipramine and nortriptyline), monoamine oxidase inhibitors (e.g., phenelzine, tranylcypromine, isocarboxasid)), generally have an excitatory effect on neural tissue. Inhibitory neurotransmitters (e.g., dopamine, glycine, and gamma-aminobutyric acid (GABA)), agonists thereof, and agents that act to increase levels of an inhibitory neurotransmitter(s) generally have an inhibitory effect (e.g., benzodiasepine (e.g., chlordiazepoxide, clonazepam, diazepam, lorazepam, oxazepam, prazepam alprazolam); flurazepam, temazepam, or triazolam). Dopamine acts as an excitatory neurotransmitter in some locations and circumstances and as an inhibitory neurotransmitter in other locations and circumstances. However, antagonists of inhibitory neurotransmitters (e.g., bicuculline) and agents that act to decrease levels of an inhibitory neurotransmitter(s) have been demonstrated to excite neural tissue, leading to increased neural activity. Similarly, excitatory neurotransmitter antagonists (e.g., prazosin, and metoprolol) and agents that decrease levels of excitatory neurotransmitters may inhibit neural activity. Yet further, lithium salts and anesthetics (e.g., lidocane, procaine, tocainide, flecainide acetate) may also be used in combination with electrical stimulation. Other pharmaceuticals that may be used include, but are not limited to, antihitstimines (e.g., chlorpheniramine, meclizine); diuretics (e.g., fjurosemide); vasoactive drugs (e.g., histamine, hydergine, vinpocetine, pentoxifyline); herbs (e.g., ginko bilboba, black cohosh, ligustrum, mullein, pulsatilla, St. Jon Wort); and vitamins and minerals (e.g., magnesium, calcium, potassium, zinc, manganese, copper, vitamin B12, beta carotene, selenium, vitamin C, vitamin E and niacin).

The pump (147) or controlled drug release device described herein may include any of a variety of different drug delivery systems. Controlled drug release devices based upon a mechanical or electromechanical infusion pump may be used. In other examples, the controlled drug release device can include a diffusion-based delivery system, e.g., erosion-based delivery systems (e.g., polymer-impregnated with drug placed within a drug-impermeable reservoir in communication with the drug delivery conduit of a catheter), electrodiffusion systems, and the like. Another example is a convective drug delivery system, e.g., systems based upon electroosmosis, vapor pressure pumps, electrolytic pumps, effervescent pumps, piezoelectric pumps and osmotic pumps. Another example is a micro-drug pump.

Exemplary pumps (147) or controlled drug release devices suitable for use as described herein include, but are not necessarily limited to, those disclosed in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,360,019; 4,487,603; 4,627,850; 4,692,147; 4,725,852; 4,865,845; 5,057,318; 5,059,423; 5,112,614; 5,137,727; 5,234,692; 5,234,693; 5,728,396; 6,368,315 and the like. Additional exemplary drug pumps suitable for use as described herein include, but are not necessarily limited to, those disclosed in U.S. Pat. Nos. 4,562,751; 4,678,408; 4,685,903; 5,080,653; 5,097,122; 6,740,072; and 6,770,067. Exemplary micro-drug pumps suitable for use as described herein include, but are not necessarily limited to, those disclosed in U.S. Pat. Nos. 5,234,692; 5,234,693; 5,728,396; 6,368,315; 6,666,845; and 6,620,151. All of these listed patents are incorporated herein by reference in their respective entireties.

The stimulator (140) of FIG. 4 is illustrative of many types of stimulators that may be used to stimulate the stimulation site within the auditory pathway to treat an auditory dysfunction. For example, the stimulator (140) may include an implantable pulse generator (IPG) coupled to one or more leads having a number of electrodes, a spinal cord stimulator (SCS), a cochlear implant, a deep brain stimulator, a drug pump (mentioned previously), a micro-drug pump (mentioned previously), or any other type of implantable stimulator configured to deliver a stimulus to a stimulation site within a patient. Exemplary IPGs suitable for use as described herein include, but are not limited to, those disclosed in the U.S. Pat. Nos. 6,381,496, 6,553,263; and 6,760,626. Another exemplary IPG is manufactured by Advanced Neuromodulation Systems, Inc., such as the GENESIS® System. Exemplary spinal cord stimulators suitable for use as described herein include, but are not limited to, those disclosed in U.S. Pat. Nos. 5,501,703; 6,487,446; and 6,516,227. Exemplary cochlear implants suitable for use as described herein include, but are not limited to, those disclosed in U.S. Pat. Nos. 6,219,580; 6,272,382; and 6,308,101. Exemplary deep brain stimulators suitable for use as described herein include, but are not limited to, those disclosed in U.S. Pat. Nos. 5,938,688; 6,016,449; and 6,539,263. All of these listed patents are incorporated herein by reference in their respective entireties.

Alternatively, the stimulator (140) may include an implantable microstimulator, such as a BION® microstimulator (ADVANCED BIONICS® Corporation, Valencia, Calif.). Various details associated with the manufacture, operation, and use of implantable microstimulators are disclosed in U.S. Pat. Nos. 5,193,539; 5,193,540; 5,312,439; 6,185,452; 6,164, 284; 6,208,894; and 6,051,017. All of these listed patents are incorporated herein by reference in their respective entireties.

Figure 6:
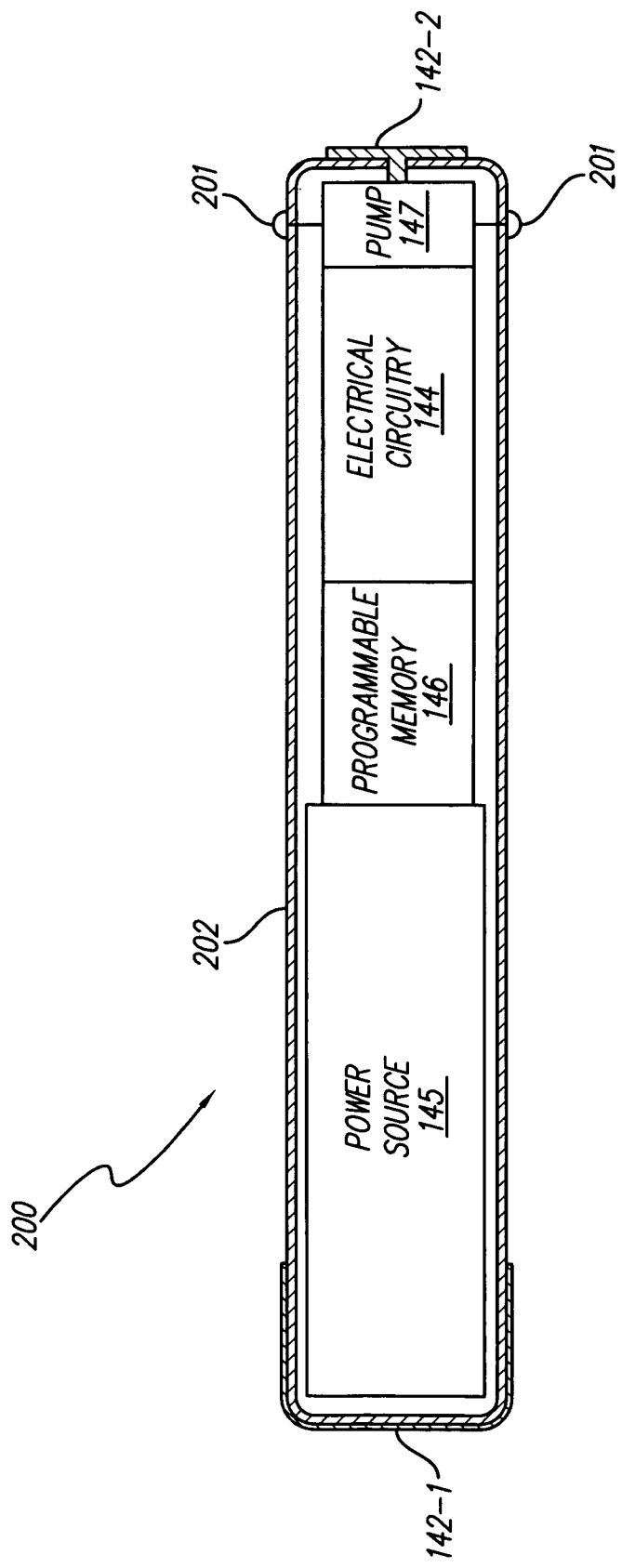
FIG. 6 illustrates an exemplary microstimulator that may be used as the stimulator according to principles described herein.

FIG. 6 illustrates an exemplary microstimulator (200) that may be used as the stimulator (140; FIG. 4) described herein. Other configurations of the microstimulator (200) are possible, as shown in the above-referenced patents and as described further below.

As shown in FIG. 6, the microstimulator (200) may include the power source (145), the programmable memory (146), the electrical circuitry (144), and the pump (147) described in connection with FIG. 4. These components are housed within a capsule (202). The capsule (202) may be a thin, elongated cylinder or any other shape as best serves a particular application. The shape of the capsule (202) may be determined by the structure of the desired target nerve, the surrounding area, and the method of implementation. In some embodiments, volume of the capsule (202) is substantially equal to or less than three cubic centimeters.

In some embodiments, the microstimulator (200) may include two or more leadless electrodes (142). Either or both of the electrodes (142) may alternatively be located at the ends of short, flexible leads as described in U.S. patent application Ser. No. 09/624,130 filed Jul. 24, 2000, now abandoned, which is incorporated herein by reference in its entirety. The use of such leads permits, among other things, electrical stimulation to be directed more locally to targeted tissue(s) a short distance from the surgical fixation of the bulk of the microstimulator (200), while allowing most elements of the microstimulator (200) to be located in a more surgically convenient site. This minimizes the distance traversed and the surgical planes crossed by the microstimulator (200) and any lead(s).

The external surfaces of the microstimulator (200) may advantageously be composed of biocompatible materials. For example, the capsule (202) may be made of glass, ceramic, metal, or any other material that provides a hermetic package that will exclude water vapor but permit passage of electromagnetic fields used to transmit data and/or power. The electrodes (142) may be made of a noble or refractory metal or compound, such as platinum, iridium, tantalum, titanium, titanium nitride, niobium or alloys of any of these, in order to avoid corrosion or electrolysis which could damage the surrounding tissues and the device.

The microstimulator (200) may also include one or more infusion outlets (201). The infusion outlets (201) facilitate the infusion of one or more drugs into a treatment site to treat a particular medical condition. The infusion outlets (201) may dispense one or more drugs directly to the treatment site. Alternatively, as will be described in more detail below, catheters may be coupled to the infusion outlets (201) to deliver the drug therapy to a treatment site some distance from the body of the microstimulator (200). The stimulator (200) of FIG. 6 also includes electrodes (142-1 and 142-2) at either end of the capsule (202). One of the electrodes (142) may be designated as a stimulating electrode to be placed close to the treatment site and one of the electrodes (142) may be designated as an indifferent electrode used to complete a stimulation circuit.

The microstimulator (200) may be implanted within a patient with a surgical tool such as a hypodermic needle, bore needle, or any other tool specially designed for the purpose. Alternatively, the microstimulator (200) may be implanted using endoscopic or laparoscopic techniques.

Figure 7:
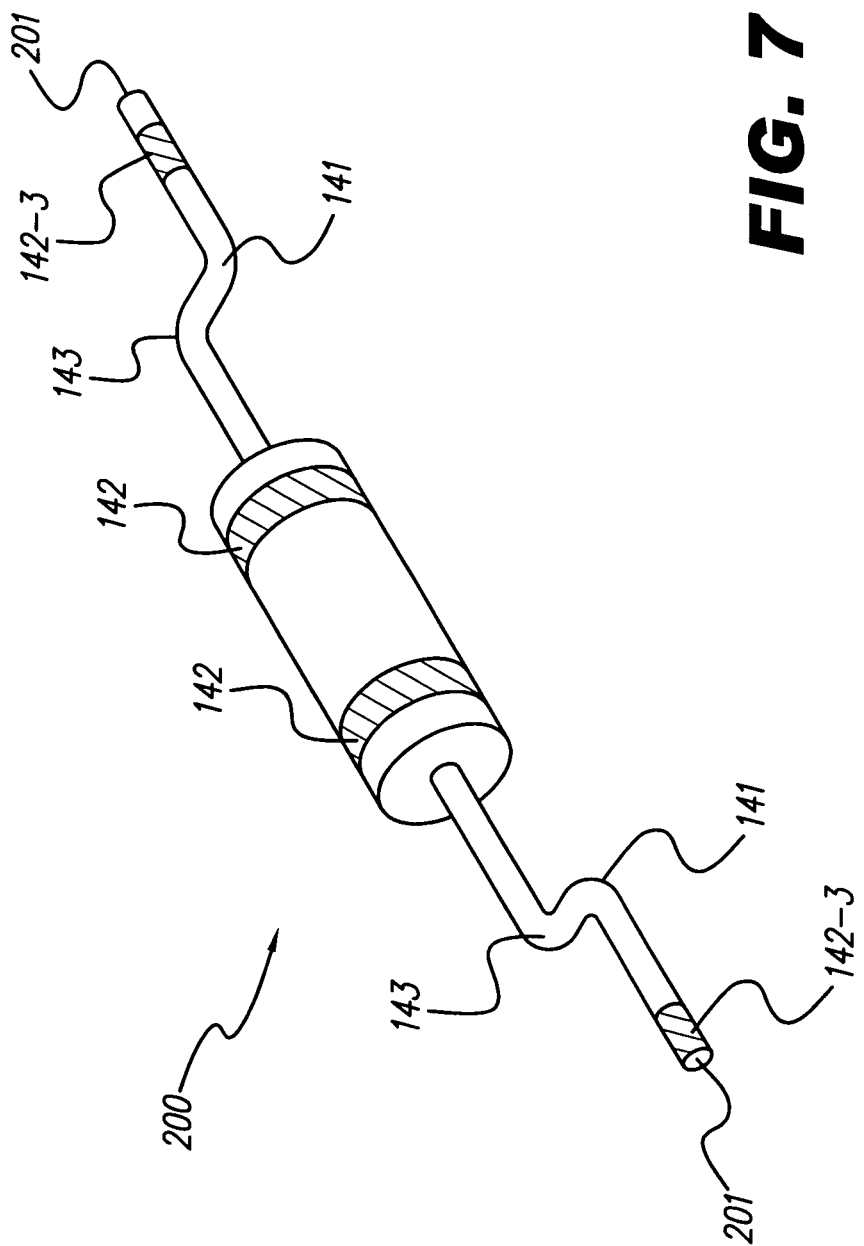
FIG. 7 shows one or more catheters coupled to the microstimulator according to principles described herein.

FIG. 7 shows an example of a microstimulator (200) with one or more catheters (143) coupled to the infusion outlets on the body of the microstimulator (200). With the catheters (143) in place, the infusion outlets (201) that actually deliver the drug therapy to target tissue are located at the ends of catheters (143). Thus, in the example of FIG. 7, a drug therapy is expelled by the pump (147, FIG. 6) from an infusion outlet (201, FIG. 6) in the casing (202, FIG. 6) of the microstimulator (200), through the catheter (143), out an infusion outlet (201) at the end of the catheter (143) to the stimulation site within the patient. As shown in FIG. 7, the catheters (143) may also serve as leads (141) having one or more electrodes (142-3) disposed thereon. Thus, the catheters (143) and leads (141) of FIG. 7 permit infused drugs and/or electrical stimulation current to be directed to a stimulation site while allowing most elements of the microstimulator (200) to be located in a more surgically convenient site. The example of FIG. 7 may also include leadless electrodes (142) disposed on the housing of the microstimulator (200), in the same manner described above.

Figure 8:
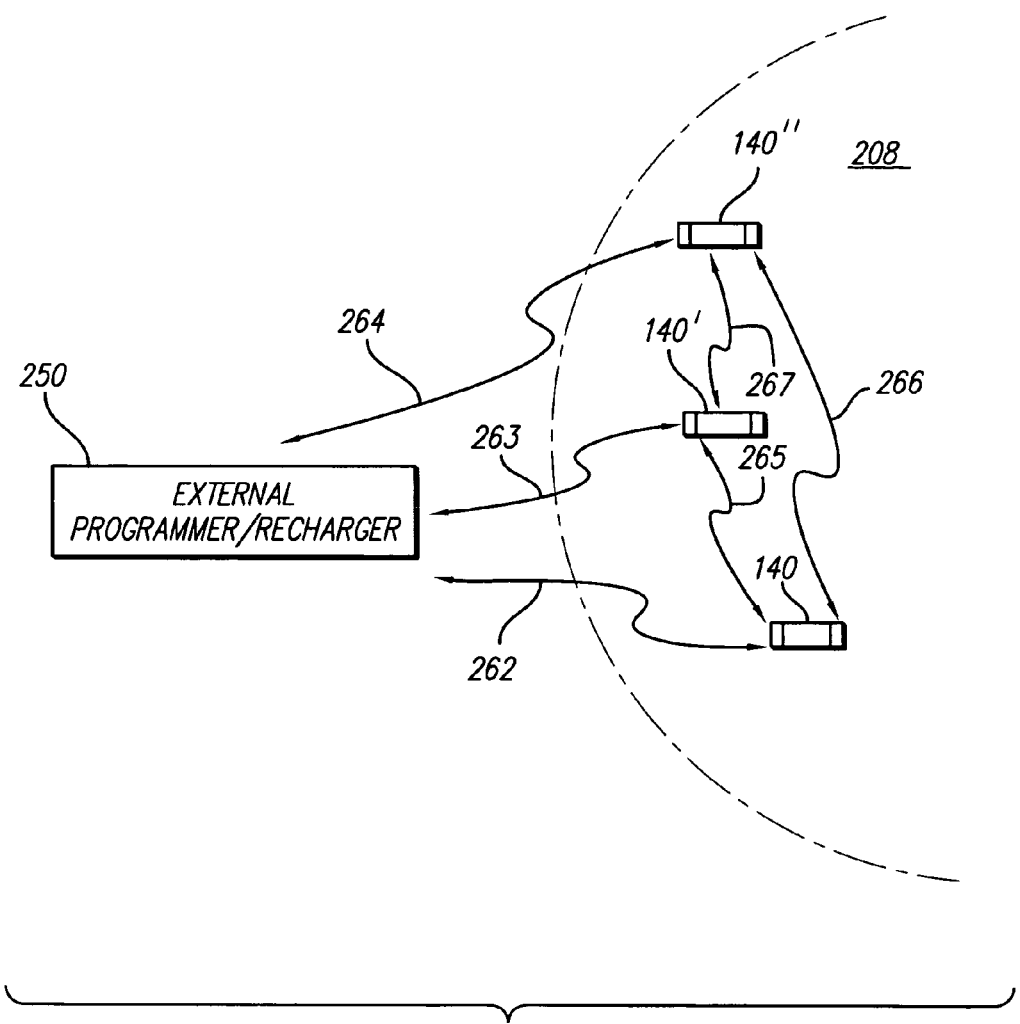
FIG. 8 depicts a number of stimulators configured to communicate with each other and/or with one or more external devices according to principles described herein.

A stimulator may be configured to operate independently. Alternatively, as shown in FIG. 8 and described in more detail below, the stimulator (140) may be configured to operate in a coordinated manner with one or more additional stimulators, other implanted devices, or other devices external to the patient's body. For instance, a first stimulator may control, or operate under the control of, a second stimulator, other implanted device, or other device external to the patient's body. The stimulator (140) may be configured to communicate with other implanted stimulators, other implanted devices, or other devices external to the patient's body via an RF link, an untrasonic link, an optical link, or any other type of communication link. For example, the stimulator (140) may be configured to communicate with an external remote control unit that is capable of sending commands and/or data to the stimulator (140) and that is configured to receive commands and/or data from the stimulator (140).

In order to determine the strength and/or duration of electrical stimulation and/or amount and/or type(s) of stimulating drug(s) required to most effectively treat an auditory dysfunction, various indicators of the auditory dysfunction and/or a patient's response to treatment may be sensed or measured. These indicators include, but are not limited to, electrical activity of the brain (e.g., EEG); chemical levels within the brain; neurotransmitter levels; hormone levels; metabolic activity in the brain; blood flow rate in the head, neck or other areas of the body; medication levels within the patient; patient input (e.g., perceived sound); temperature of tissue in stimulation target region; and brain hyperexcitability, e.g. increased response of given tissue to the same input. In some embodiments, the stimulator (140) may be configured to change the stimulation parameters in a closed loop manner in response to these measurements. The stimulator (140) may be configured to perform the measurements. Alternatively, other sensing devices may be configured to perform the measurements and transmit the measured values to the stimulator (140). Exemplary sensing devices include, but are not limited to, chemical sensors, electrodes, optical sensors, and temperature sensors.

Thus, one or more external devices may be provided to interact with the stimulator (140), and may be used to accomplish at least one or more of the following functions:

Function 1: If necessary, transmit electrical power to the stimulator (140) in order to power the stimulator (140) and/or recharge the power source (145).

Function 2: Transmit data to the stimulator (140) in order to change the stimulation parameters used by the stimulator (140).

Function 3: Receive data indicating the state of the stimulator (140) (e.g., battery level, drug level, stimulation parameters, etc.).

Additional functions may include adjusting the stimulation parameters based on information sensed by the stimulator (140) or by other sensing devices.

By way of example, an exemplary method of treating a patient with an auditory dysfunction may be carried out according to the following sequence of procedures. The steps listed below may be modified, reordered, and/or added to as best serves a particular application.

1. A stimulator (140) is implanted so that its electrodes (142) and/or infusion outlet (149) are in communication with a stimulation site along the auditory pathway.

2. The stimulator (140) is programmed to apply at least one stimulus to the stimulation site. The stimulus may include electrical stimulation, drug stimulation, chemical stimulation, thermal stimulation, electromagnetic stimulation, mechanical stimulation, and/or any other suitable stimulation.

3. When the patient desires to invoke stimulation, the patient sends a command to the stimulator (140) (e.g., via a remote control) such that the stimulator (140) delivers the prescribed stimulation. The stimulator (140) may be alternatively or additionally configured to automatically apply the stimulation in response to sensed indicators of an auditory dysfunction.

4. To cease stimulation, the patient may turn off the stimulator (140) (e.g., via a remote control).

5. Periodically, the power source (145) of the stimulator (140) is recharged, if necessary, in accordance with Function 1 described above. As will be described below, this recharging function can be made much more efficient using the principles disclosed herein.

In other examples, the treatment administered by the stimulator (140), i.e., drug therapy and/or electrical stimulation, may be automatic and not controlled or invoked by the patient.

For the treatment of different patients with auditory dysfunctions, it may be desirable to modify or adjust the algorithmic functions performed by the implanted and/or external components, as well as the surgical approaches. For example, in some situations, it may be desirable to employ more than one stimulator (140), each of which could be separately controlled by means of a digital address. Multiple channels and/or multiple patterns of stimulation may thereby be used to deal with the various components of auditory dysfunctions, such as the combination of auditory hallucinations with another form of an auditory dysfunction, e.g., tinnitus.

As shown in the example of FIG. 8, a first stimulator (140) implanted beneath the skin of the patient (208) provides a stimulus to a first location; a second stimulator (140') provides a stimulus to a second location; and a third stimulator (140") provides a stimulus to a third location. As mentioned earlier, the implanted devices may operate independently or may operate in a coordinated manner with other implanted devices or other devices external to the patient's body. That is, an external controller (250) may be configured to control the operation of each of the implanted devices (140, 140', and 140"). In some embodiments, an implanted device, e.g. stimulator (140), may control, or operate under the control of, another implanted device(s), e.g. stimulator (140') and/or stimulator (140"). Control lines (262-267) have been drawn in FIG. 8 to illustrate that the external controller (250) may communicate or provide power to any of the implanted devices (140, 140', and 140") and that each of the various implanted devices (140, 140', and 140") may communicate with and, in some instances, control any of the other implanted devices.

As a further example of multiple stimulators (140) operating in a coordinated manner, the first and second stimulators (140, 140') of FIG. 8 may be configured to sense various indicators of an auditory dysfunction and transmit the measured information to the third stimulator (140"). The third stimulator (140") may then use the measured information to adjust its stimulation parameters and apply stimulation to a stimulation site accordingly. The various implanted stimulators may, in any combination, sense indicators of an auditory dysfunction, communicate or receive data on such indicators, and adjust stimulation parameters accordingly.

Alternatively, the external device (250) or other external devices communicating with the external device may be configured to sense various indicators of a patient's condition. The sensed indicators can then be collected by the external device (250) for relay to one or more of the implanted stimulators or may be transmitted directly to one or more of the implanted stimulators by any of an array of external sensing devices. In either case, the stimulator, upon receiving the sensed indicator(s), may adjust stimulation parameters accordingly. In other examples, the external controller (250) may determine whether any change to the stimulation parameters is needed based on the sensed indicators. The external device (250) may then signal a command to one or more of the stimulators to adjust stimulation parameters accordingly.

The stimulation sites along the auditory pathway that may be stimulated to treat an auditory dysfunction include, for example, but are not limited to, the cochlear nuclei, auditory striae, superior olivary complex, lateral lemniscus, inferior colliculus, brachium of the inferior colliculus, medial geniculate body, primary auditory cortex, secondary auditory cortical area, and auditory radiations. However, additional or alternative sites within the brain may be stimulated to treat auditory dysfunctions as best serves a particular application.

Figure 9:
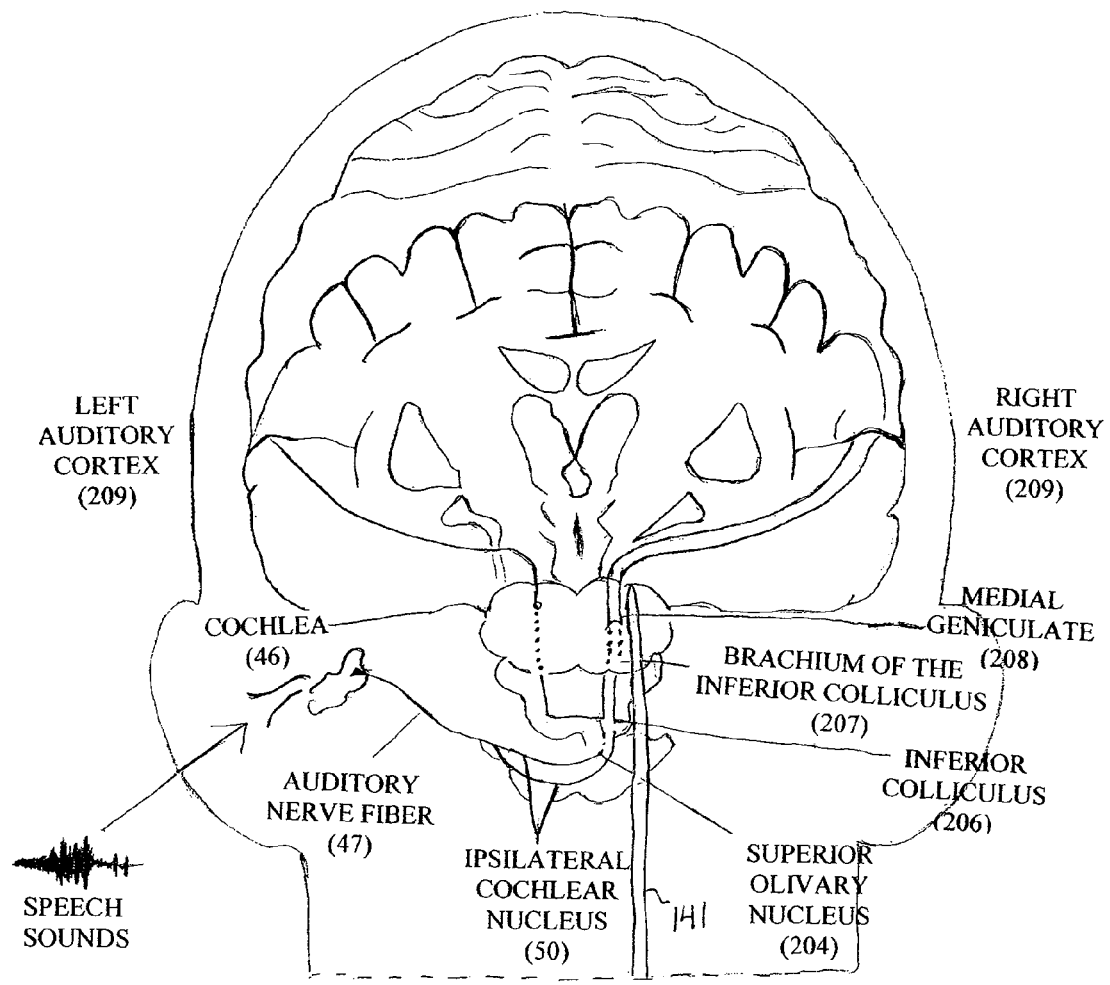
FIG. 9 illustrates an exemplary lead that is implanted adjacent to a stimulation site within the brain according to principles described herein.

FIG. 9 illustrates an exemplary lead (141) that is implanted adjacent to a stimulation site within the brain. The stimulation site in FIG. 9 is the brachium of the inferior colliculus (207) for illustrative purposes only. As shown in FIG. 9, the lead (141) is in communication with the stimulation site (207). As used herein and in the appended claims, the term "in communication with" refers to the stimulation lead (141) and/or catheter being adjacent, in the general vicinity, in close proximity, or directly next to or directly on the stimulation site such that stimulation can be effectively delivered. Thus, the lead (141) and/or catheter is "in communication with" the stimulation site if the stimulation results in a modulation of neuronal activity.

By way of example, a method of implanting a lead (141) in communication with a stimulation site within the brain to treat an auditory dysfunction may be carried out according to the following sequence of procedures. The steps listed below may be modified, reordered, and/or added to as best serves a particular application.

1. A patient who is to have a stimulation lead implanted to stimulate a stimulation site within the brain, generally, first has a stereotactic head frame, such as the Leksell, Cosman-Robert-Wells (CRW), or Compass, mounted to his or her skull by fixed screws. However, frameless techniques may also be used.

2. Subsequent to the mounting of the frame, the patient may undergo a series of magnetic resonance imaging sessions, during which a series of two dimensional slice images of the patient's brain are built up into a quasi-three dimensional map in virtual space. This map is then correlated to the three dimensional stereotactic frame of reference in the real surgical field. In order to align these two coordinate frames, the head frame may be rigidly mounted to the surgical table.

Subsequently, a series of reference points are established to relative aspects of the frame and patient's skull, so that either a person or a computer software system can adjust and calculate the correlation between the patient's head and the virtual space model of the patient MRI scans. The surgeon is then able to target any region within the stereotactic space of the brain with precision (e.g., within 1 mm).

3. Initial anatomical target localization is achieved either directly using the MRI images, or indirectly using interactive anatomical atlas programs that map the atlas image onto the stereotactic image of the brain. Alternative mapping techniques may be used as best serves a particular application.

4. The position of the predetermined target stimulation sites in the auditory pathway may then be derived. Based upon the derived coordinates, the electrical stimulation lead (141) is positioned in the brain. Typically, an insertion cannula for the electrical stimulation lead (141) is inserted through a burr hole in the skull into the brain, but a cannula is not required. For example, a hollow needle may provide the cannula. The cannula and electrical stimulation lead (141) may be inserted together or the lead (141) may be inserted through the cannula after the cannula has been inserted.

5. The position of the lead (141) is confirmed by evoking sound perceptions with electrical stimulation of the brain. This can be achieved using microstimulation (50-100 Hz, 100 microseconds pulse width and 1-100 microamps using a microelectrode with an impedance of 0.1-1.0 megaohm) or with macrostimulation with electrodes with a lower impedance using similar stimulation parameters but higher currents (0.1-10 milliamperes). Patients being stimulated along the auditory pathways typically report hearing a "buzzing," "bee humming," or "cricket" sound in their ear.

6. Once the electrical stimulation lead (141) has been positioned in the brain, the lead (141) is uncoupled from any stereotactic equipment present, and the cannula and stereotactic equipment are removed. Where appropriate, any burr hole cover seated in the burr hole may be used to secure the electrical stimulation lead (141) in position and possibly to help prevent leakage from the burr hole and entry of contaminants into the burr hole.

7. Once the lead (141) has been inserted and secured, the proximal portion of the lead (141) is extended from the lead insertion site to the implant site where the stimulator (140) is implanted and coupled to the stimulator (140). The implant site is typically a subcutaneous pocket formed to receive and house the stimulator (140) and may be positioned a distance away from the insertion site, such as near the chest, below the clavicle, or alternatively near the buttocks or another place in the torso area.

In some examples, where the primary cortex or secondary cortical areas are to be stimulated, the lead (141) and/or stimulator (140) are placed epidurally. In some alternative examples, the lead (141) and/or stimulator (140) are placed in the subdural space.

The application of one or more stimuli to a stimulation site along the auditory pathway may treat auditory dysfunctions by driving, blocking or disrupting the transmission of auditory information. For example, some auditory dysfunctions may be treated by producing perceived sounds and/or tones that superpose and/or ameliorate the sounds that are perceived by the patient.

The preceding description has been presented only to illustrate and describe embodiments of the invention. It is not intended to be exhaustive or to limit the invention to any precise form disclosed. Many modifications and variations are possible in light of the above teaching.

What is claimed is:

1. A method of treating an auditory dysfunction, said method comprising:
   applying at least one stimulus to a stimulation site within a patient with an implanted stimulator in accordance with one or more stimulation parameters to treat said auditory dysfunction;
   wherein said auditory dysfunction comprises at least one or more of auditory hallucinations, hyperacusis, schizophrenia, and phonophobia;
   wherein said stimulation site comprises at least one or more of a cochlear nucleus, auditory striae, superior olivary complex, lateral lemniscus, inferior colliculus, brachium of the inferior colliculus, medial geniculate body, primary auditory cortex, secondary auditory cortical area, and auditory radiation; and
   wherein said stimulation site comprises a cochlear nucleus.

2. A method of treating an auditory dysfunction, said method comprising:
   applying at least one stimulus to a stimulation site within a patient with an implanted stimulator in accordance with one or more stimulation parameters to treat said auditory dysfunction;
   wherein said auditory dysfunction comprises at least one or more of auditory hallucinations, hyperacusis, schizophrenia, and phonophobia;
   wherein said stimulation site comprises at least one or more of a cochlear nucleus, auditory striae, superior olivary complex, lateral lemniscus, inferior colliculus, brachium of the inferior colliculus, medial geniculate body, primary auditory cortex, secondary auditory cortical area, and auditory radiation; and
   wherein said stimulation site comprises an auditory striae.

3. A method of treating an auditory dysfunction, said method comprising:
   applying at least one stimulus to a stimulation site within a patient with an implanted stimulator in accordance with one or more stimulation parameters to treat said auditory dysfunction;
   wherein said auditory dysfunction comprises at least one or more of auditory hallucinations, hyperacusis, schizophrenia, and phonophobia;
   wherein said stimulation site comprises at least one or more of a cochlear nucleus, auditory striae, superior olivary complex, lateral lemniscus, inferior colliculus, brachium of the inferior colliculus, medial geniculate body, primary auditory cortex, secondary auditory cortical area, and auditory radiation; and
   wherein said stimulation site comprises an auditory radiation.

* * * * *